United States Patent

Ichioka et al.

(10) Patent No.: US 6,461,627 B1
(45) Date of Patent: Oct. 8, 2002

(54) SKIN PREPARATIONS FOR EXTERNAL USE

(75) Inventors: Minoru Ichioka; Toshiro Sone; Tomoko Hanamizu; Makoto Ohwaki; Katsuyoshi Chiba; Koji Miyazaki; Yoshio Hiraki; Satoshi Yoshikawa, all of Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 0 days.

(21) Appl. No.: 09/787,928
(22) PCT Filed: Oct. 5, 1999
(86) PCT No.: PCT/JP99/05474
§ 371 (c)(1),
(2), (4) Date: Apr. 3, 2001
(87) PCT Pub. No.: WO00/21501
PCT Pub. Date: Apr. 20, 2000

(30) Foreign Application Priority Data

Oct. 9, 1998 (JP) .............................. 10-287895

(51) Int. Cl.[7] .......................... A61K 6/00; A61K 35/00; A61K 35/78; A01N 63/00
(52) U.S. Cl. .................... 424/401; 424/93.45; 424/114; 424/758
(58) Field of Search .............................. 424/401, 93.45, 424/758, 114

(56) References Cited

U.S. PATENT DOCUMENTS

| | | | |
|---|---|---|---|
| 4,218,489 A | * | 8/1980 | Zilliken ........................ 426/545 |
| 4,464,362 A | * | 8/1984 | Kludas et al. ............... 424/114 |
| 5,164,183 A | * | 11/1992 | Komoda et al. ............. 424/758 |
| 5,824,702 A | * | 10/1998 | Wei .............................. 424/59 |
| 6,258,355 B1 | * | 7/2001 | Cavaliere widow Veseley et al. .......... 424/93.45 |

FOREIGN PATENT DOCUMENTS

| | | |
|---|---|---|
| JP | 06-065041 | 3/1994 |
| JP | 06-128140 | 5/1994 |
| JP | 10-287540 | 10/1998 |
| WO | WO 82/00093 | 1/1998 |

OTHER PUBLICATIONS

Kikuchi–Hayakawa et al, "Effects of soya milk and Bifido-bacterium–fermented soya milk on plasma and liver lipids, and faecal steroids in hamsters fed on a cholesterol–free or cholesterol–enriched diet" British Journal of Nutrition (1998) 79, 97–105.*

Scalabrini et al, "Characterization of Bifidobacterium strains for use in soymilk fermentation" International Journal of Food Microbiology (1998) 39, 213–219.*

Matsuyama et al, "Fermentation Profiles and Utilization of Sugars of Bifidobacteria in Soymilk," Journal of the Japanese Societ for Food Science and Technology (1992) 39, 887–893.*

* cited by examiner

Primary Examiner—Michael G. Hartley
Assistant Examiner—Michael A. Willis
(74) Attorney, Agent, or Firm—Oblon, Spivak, McClelland, Maier & Neustadt, P.C.

(57) ABSTRACT

Skin preparations for external use and cosmetics which contain a fermented soybean extract prepared by extracting with an organic solvent a fermentation product obtained by treating a soybean extract with one or more microorganisms selected from bifidobacteria. These preparations are excellent in the effects of relieving wrinkles and ameliorating rough skin.

8 Claims, 2 Drawing Sheets

SKIN PREPARATIONS FOR EXTERNAL USE

This is a 371 of PCT/JP99/05474, submitted Oct. 5, 1999.

1. Technical Field

The present invention relates to a skin preparation for external use and cosmetics which exhibit excellent effects of ameliorating roughening of the skin and retarding aging of the skin.

2. Background Art

Hitherto, application of soybean extract or soymilk—which is a specific type of soybean extract—to cosmetics has been known, and a number of reports have confirmed its whitening effect. Of such applications, example applications of a fermentation product of soymilk (hereinafter referred to as fermented soymilk) in the field of cosmetics include cosmetics making use of the action of a microorganism belonging to genus Rhizopus (Japanese Patent Application No. 1-102011) and those making use of the action of lactic acid bacteria (Japanese Patent Application No. 3-127713).

However, no published report has mentioned that fermented soymilk is effective in retarding wrinkle formation caused by aging or UV rays, or in ameliorating roughening of the skin.

Accordingly, an object of the present invention is to provide a skin preparation for external use which can ameliorate such conditions of roughening of the skin and formation of wrinkles.

Disclosure of the Invention

In view of the foregoing, the present inventors have conducted extensive researches, and quite surprisingly, have found that when a fermentation product obtained by causing a microorganism belonging to genus Bifidobacterium to act on a soybean extract is subjected to extraction with an organic solvent, there can be obtained a fermented soybean extract which can ameliorate such conditions of roughening of the skin and formation of wrinkles, thus leading to completion of the invention.

Accordingly, the present invention provides a skin preparation for external use which contains a fermented soybean extract prepared by extracting with an organic solvent a fermentation product obtained by treating a soybean extract with one or more microorganisms selected from bifidobacteria.

BEST MODES FOR CARRYING OUT THE INVENTION

Figure 1:
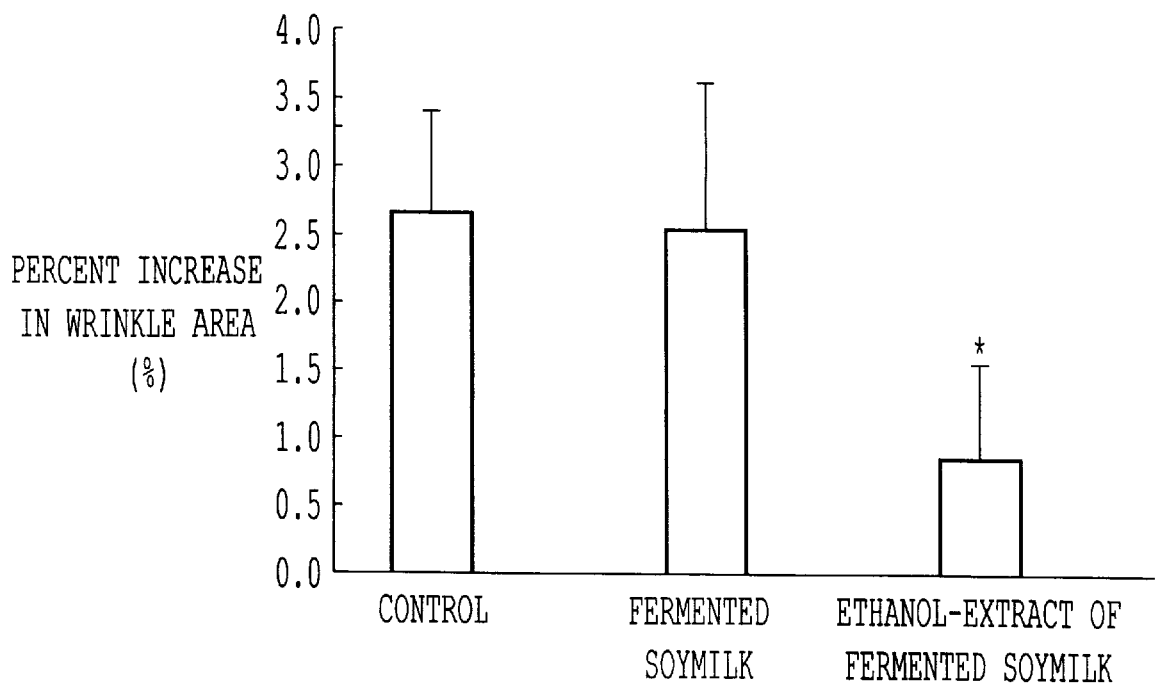
FIG. 1 is a graph showing the effect of a fermented soymilk extract on formation of wrinkles [*: statistically significant as compared with fermented soymilk ($p<0.05$, n=5)].

The fermented soybean extract used in the skin preparation for external use of the present invention is prepared by extracting, with an organic solvent, a fermentation product obtained by causing bifidobacteria to fact on a soybean extract. Preferably, the soybean extract is soymilk, which is an extract of soybeans in water.

The following are example steps for preparing the skin preparation for external use of the present invention from soymilk.

(1) Production of Soymilk (Step 1)

The soymilk to be used in the present invention may be produced through any method. For example, soybeans serving as a starting material are soaked in water, then hot water or hot water containing 0.5–1.0% by weight sodium carbonate is added thereto and the mixture is ground, bean-curd refuse is discarded, and the remaining solution is sterilized under heat. Generally, soymilk having a solid content of about 10% is used.

The soybeans serving as the starting material of the soymilk used in the present invention are not particularly limited. Preferably, whole soybeans containing oils and fats, skin-removed soybeans, or soybean flakes are preferred, with skin-removed soybeans being particularly preferred.

To the resultant soymilk, there may be added a variety of additives which include, for the subsequent microorganism treatment step, sucrose, glucose, fructose, invert sugar, and other sugars used in foods; and meat extract, yeast extract, peptone, peptide, and other nutrients which are required for the growth of microorganisms. In order to adjust the pH of the soymilk to a value optimal for the growth of microorganisms, citric acid, malic acid, ascorbic acid, lactic acid, acetic acid, or similar acids used in foods may be added to the soymilk.

(2) Fermentation of Soybeans (Step 2)

The method for causing a microorganism to act on the soymilk produced in step 1 above is not particularly limited. For example, cell suspension of cultured microorganism is inoculated in the above-described soymilk, followed by fermentation under conditions, including time and temperature, suitable for the microorganism (generally temperature is 20–39° C. in the case of bifidobacteria). The culture may be performed either with stirring or without stirring. Fermentation may be a mixed fermentation in which a plurality of microorganism strains are combined, or a continuous fermentation in which a plurality of microorganism strains are serially combined.

The microorganisms which belong to genus Bifidobacterium and which may be caused to act on a soybean extract are not particularly limited. For example, *Bifidobacterium breve, Bifidobacterium bifidum, Bifidobacterium longum, Bifidobacterium adolescentis*, or *Bifidobacterium infantis* may be used. These may be used solely or in combination of two or more species. Together with any of these microorganisms, other types of lactic acid bacteria, e.g., those belonging to genus Lactobacillus, Streptococcus, Lactococcus, and Enterococcus, may be used to proceed fermentation, and the resultant fermentation products may be utilized.

(3) Extraction of Fermentation Product (step 3)

The organic solvent for extracting the fermentation product obtained in step 2 is not particularly limited. Example organic solvents include C1–C13 monovalent or polyvalent alcohols, hexane, benzene, acetone, ethyl acetate, dimethylsulfoxide, and ether. Specific examples include lower alcohols (monovalent alcohols) such as methanol and ethanol; and polyvalent alcohols such as polyethylene glycol, propylene glycol, 1,3-butylene glycol, isoprene glycol, and glycerol. Extraction of the fermentation product with an organic solvent provides components which ameliorate wrinkle formation and skin roughening and which elevate the hyaluronic acid content of the skin.

It should be noted that, depending on the species of the solvent used for extracting the fermentation product, the amounts of extractable active components effective to prevent skin roughening and the amounts of foul-odor-issuing components (volatile components) differ. That is, when a low-molecular-weight solvent or a solvent having a single hydroxyl group in the molecule is used, volatile components issuing a foul odor are extracted in greater amounts, thereby reducing the amount of the extract as a raw material of cosmetics or similar products. In contrast, when a high-molecular-weight solvent is used, the extractable amounts of active components somewhat decrease, and in some cases, such a high-molecular-weight solvent yields stickiness when incorporated into cosmetics or similar products.

Therefore, the solvent for extraction is preferably a C3–C13 polyhydric alcohol. Use of such a solvent provides an extract which has minimized foul odor and which promises excellent sensation in use. Specific examples of such a polyhydric alcohol include 1,3-butylene glycol, glycerol, propylene glycol, and isoprene glycol. These may be used solely or in combination. As used herein, a polyhydric alcohol is an alcohol having two or more hydroxyl groups in one molecule. Polyhydric alcohols prepared by any method may be used in the present invention.

When extraction is carried out through use of such an organic solvent, 0.01–100 parts by weight of an organic solvent is added to one part by weight of a fermentation product, and then the mixture is subjected to filtration or centrifugal separation, to thereby remove highly polar substances. The extraction temperature may be any temperature between 4° C. and the boiling point of each single solvent or a solvent mixture. The extraction time is preferably 15 minutes to about 48 hours.

When the thus-produced extract of a fermentation product is used as a skin preparation for external use, the extract may be directly used in solution form. Alternatively, the extract may further be subjected to centrifugal separation, filtration, or similar means so as to remove insoluble matter, and the thus-prepared solution may be used. Subsequently, this solution may be subjected to evaporation to dryness, heating to dryness, or air-drying, and the resultant concentrated solution or solid product may be used. Moreover, the solution may be diluted with water, alcohol, or a similar material, and such diluted solution may be used. The amount of the extract or extract-derived solution, solid, etc. is preferably 0.005–50% by weight, particularly preferably 0.01–10% by weight, as reduced to the solid content of the extract. Amounts less than 0.005% by weight may fail to provide satisfactory rough skin ameliorating effect, whereas amounts exceeding 50% by weight may result in a somewhat peculiar bean odor attributable to soymilk.

The skin preparations for external use according to the present invention may be therapeutic external drugs or cosmetic compositions. Of these, cosmetic compositions are preferred. Particularly, cosmetic compositions for retarding aging of the skin and cosmetic compositions for ameliorating rough skin are preferred.

When the cosmetic compositions of the present invention further contain mucopolysaccharides such as hyaluronic acid; glycerol; culture solutions prepared by inoculating lactic acid bacteria into soymilk; culture solutions of lactic acid bacteria using milk ingredients; or humectants such as pyrrolidone carboxylic acid, α-hydroxy acid, and trimethylglycine, moisture-retaining effect of the compositions can be enhanced. Of the listed humectants, hyaluronic acid is particularly preferred.

The cosmetic compositions of the present invention may also contain known cosmetic ingredients so long as they do not impede the effect of the present invention. Such known cosmetic ingredients include, but are not limited to, water, alcohols, oily ingredients, surfactants, water-soluble polymers, vitamins, preservatives, perfumes, and colorants.

The cosmetic compositions of the present invention may be produced by a routine method. They may be formed into lotions, milky lotions, moisturizing creams, cleansing creams, massage creams, face-cleansing creams, packs, beauty lotions, or other forms.

EXAMPLES

The present invention will next be described in more detail by way of examples, which should not be construed as limiting the invention thereto.

Example 1

Soybeans were washed with water, and soaked in water overnight, to thereby cause the soybeans to absorb water sufficiently. To the water-soaked soybeans was added water in an amount four times that of soybeans, and the mixture was milled by use of a mixer, to thereby yield a paste. The paste was heated at 100° C. for 30 min, and cooled, followed by filtration, to thereby yield soymilk. The soymilk was sterilized at 100° C. for 90 min in an autoclave, to thereby yield raw soymilk for fermentation. A cell suspension containing a pre-incubated *Bifidobacterium breve* FERM P-15488 strain was inoculated into the raw soymilk for fermentation, and the inoculated soymilk was incubated at 37° C. for 24 hours without stirring culture, to thereby yield fermented soymilk.

Ethanol or 1,3-butyleneglycol (300 ml) was added to the fermented soymilk (100 ml) obtained in the above-described manner, and the mixture was stirred at room temperature for 24 hours, followed by centrifugation at 9000 rpm for 30 min. The resultant precipitates were removed. The fermented soymilk extract obtained by the extraction with ethanol was dried under vacuum, and the thus-obtained extract (2.3 g) was dissolved in 50% ethanol (100 ml), to thereby yield an application sample.

Example 2

Soybeans were washed with water, and soaked in water overnight, to thereby cause the soybeans to absorb water sufficiently. To the water-soaked soybeans was added water in an amount four times that of soybeans, and the mixture was milled by use of a mixer, to thereby yield a paste. The paste was heated at 100° C. for 30 min, and cooled, followed by filtration, to thereby yield soymilk.

The soymilk was sterilized at 100° C. for 90 min in an autclave, to thereby yield raw soymilk for fermentation. A cell suspension containing a pre-incubated *Bifidobacterium breve* FERM P-15488 strain was inoculated into the raw soymilk for fermentation, and the inoculated soymilk was incubated at 37° C. for 24 hours without stirring culture, to thereby yield fermented soymilk.

Ethanol (100 ml each) was added to each of the soymilk (100 ml) and the fermented soymilk (100 ml) obtained in the above-described manner. Each of the thus-obtained mixtures was stirred and centrifuged as described in Example 1, to thereby yield an extract of the soymilk and an extract of the fermented soymilk. The thus-obtained extracts were used as samples to be applied to the skin.

Test Example 1

The fermented soymilk extract obtained by extraction with ethanol and the fermented soymilk (before undergoing extraction), each of which was prepared in Example 1, were used as samples, and the amelioration effects on skin surface configuration were investigated. In accordance with the method of Kiss et al. (Photochem. Photobiol. 53, 109. 1991), the skin of hairless mice was irradiated with UV rays, and each of the samples was applied to the skin of the mice at a dose of 10 $\mu l/cm^2$/day every day for four weeks. The configuration of wrinkles was quantified through image analysis. Percent increase of the wrinkle area on the basis of the entire skin area subjected to the measurement was calculated. The results are shown in FIG. 1.

As shown in FIG. 1, the fermented soymilk extract of the present invention exhibits an excellent wrinkle reversal effect as compared with the results obtained from the control group (sample was not applied) or from the group of mice to which non-extracted material was applied. Thus, the fermented soymilk extract was proven to be useful as a skin paging retarding agent.

Tests similar to those described above were performed, except that 1,3-butyleneglycol was used instead of ethanol. The results obtained are almost comparable to those obtained from the case in which ethanol was used for extraction.

TABLE 1

Table of Sensory Evaluation Criteria in terms of Smell and Sensation in Use

| Sensory evaluation in terms of smell (Smell of volatile components) | Sensory evaluation in terms of sensation in use (Stickiness, etc.) | Rating |
|---|---|---|
| Very strong smell | Very poor sensation in use | 4 |
| Strong smell | Somewhat poor sensation in use | 3 |
| Moderate | Moderate | 2 |
| Tint of smell | Somewhat favorable sensation in use | 1 |
| No smell | Excellent sensation in use | 0 |

Test Example 2

Samples similar to those used in Test Example 1 were applied onto similar mice, to thereby quantify the skin furrow-crest counts through image analysis. The decrease in the skin furrow-crest count by UV irradiation is shown. The results are shown in FIG. 2.

Figure 2:
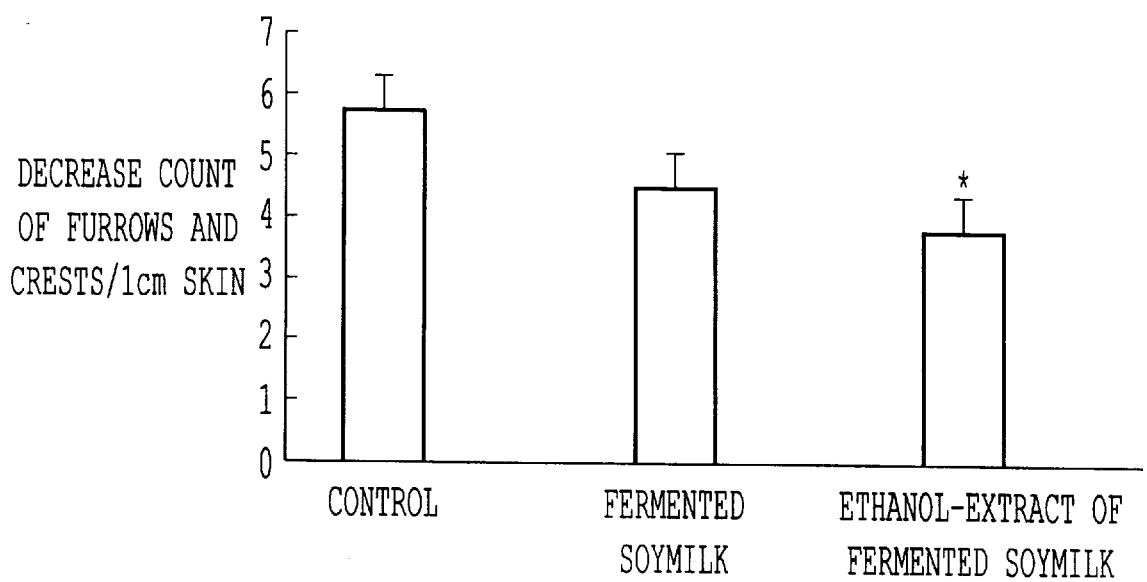
FIG. 2 is a graph showing the effect of a fermented soymilk extract on the decrease count of furrow-crest of skin [*: statistically significant as compared with fermented soymilk ($p<0.05$, n=5)].

As is apparent from FIG. 2, the ethanol extract of the fermented soymilk exhibits an excellent texture ameliorating effect as compared with the results obtained from the control group (sample was not applied) or from the group of mice to which non-extracted material was applied. Thus, the ethanol extract of the fermented soymilk was proven to be useful as a cosmetic composition for ameliorating rough skin.

Tests similar to those described above were performed, except that 1,3-butyleneglycol was used instead of ethanol. The results obtained are almost comparable to those obtained from the case in which ethanol was used for extraction.

Test Example 3

Smells of the extracted components obtained by extracting fermented soymilk with a variety of organic solvents and effects of the obtained active ingredients on the sensation during use were investigated.

Each of a variety of solvents shown in Table 2 was added to fermented soymilk (1:1 by volume), and the resultant mixture was left to stand overnight, followed by filtration. The smells of the mixtures were assessed by sensory evaluation, and analysis of active ingredients was performed. Regarding the sensory evaluation of smells, ten panelists participated in a blind test on randomized samples. The evaluation was on an absolute basis and performed in accordance with the evaluation criteria shown in Table 1. The ratings were averaged. Fermented soymilk was used as a comparative sample.

TABLE 2

Smells of Extracted Components Obtained by Extracting Fermented Soymilk with a Variety of Organic Solvents, and Effects Exerted on the Sensation During Use

| Extraction solvent | Carbon number | CS | IS 2 | IS 3 | IS 4 | IS 5 | IS 6 | IS 7 | IS 8 | IS 9 |
|---|---|---|---|---|---|---|---|---|---|---|
| Methanol | 1 | | 50% | | | | | | | |
| Ethanol | 2 | | | 50% | | | | | | |
| Poly-glycerol | 6 | | | | 50% | | | | | |
| PEG 600 | 14 | | | | | 50% | | | | |
| PEG 1540 | 37 | | | | | | 50% | | | |
| Propylene glycol | 3 | | | | | | | 50% | | |
| 1,3-butylene glycol | 4 | | | | | | | | 50% | |
| Glycerol | 3 | | | | | | | | | 50% |
| Fermented soymilk | | 100% | 50% | 50% | 50% | 50% | 50% | 50% | 50% | 50% |
| Rating of sensory evaluation of smell | | 3.8 | 3.0 | 2.9 | 1.9 | 2.2 | 2.2 | 1.8 | 1.6 | 1.7 |

TABLE 2-continued

Smells of Extracted Components Obtained by
Extracting Fermented Soymilk with a Variety of
Organic Solvents, and Effects Exerted on the
Sensation During Use

| Extraction solvent | Carbon number | CS | IS 2 | IS 3 | IS 4 | IS 5 | IS 6 | IS 7 | IS 8 | IS 9 |
|---|---|---|---|---|---|---|---|---|---|---|
| Rating of sensory evaluation of sensation in use | | 3.5 | 1.1 | 1.0 | 2.5 | 3.3 | 3.6 | 0.5 | 0.4 | 0.5 |
| Total | | 7.3 | 4.1 | 3.9 | 4.4 | 5.5 | 5.8 | 2.3 | 2.0 | 2.2 |
| Overall Evaluation | | x | Δ | Δ | Δ | x | x | ○ | ○ | ○ |

CS: Comparative sample
IS: Inventive sample
PEG: Polyethylene glycol

As is apparent from Table 2, when extraction was performed by use of propylene glycol, 1,3-butylene glycol, or glycerol, high scores were obtained in terms of both smell and sensation in use.

Test Example 4

To the skin of hairless mice, either an ethanol extract of fermented soymilk prepared in Example 2 or an ethanol extract of soymilk (both having a solid content of 1.7% by weight) was applied in an amount of 100 μl/5 cm$^3$/mouse for 2 weeks, and the effect of application on the hyaluronic acid content of the skin of the hairless mice was investigated. The control was 50% ethanol solution. Samples employed were fermented soymilk extracts (50% by weight (dilution was performed using 50% ethanol) and 100% by weight) and a soymilk extract (100% by weight). After 24 hours following the final application, the skin was extirpated, and in accordance with the method described by Hashizume et al. (Journal of JAPAN Oil Chemists' Society 46, 985–989, 1997), hyaluronic acid fraction was obtained from the skin. The hyaluronic acid content was determined by means of ELISA-like method (Fosang, A. J., et al., Matrix, 10, 306–313, 1990) employing biotin-labeled hyaluronic acid binding protein (Seikagaku Corporation).

Figure 3:
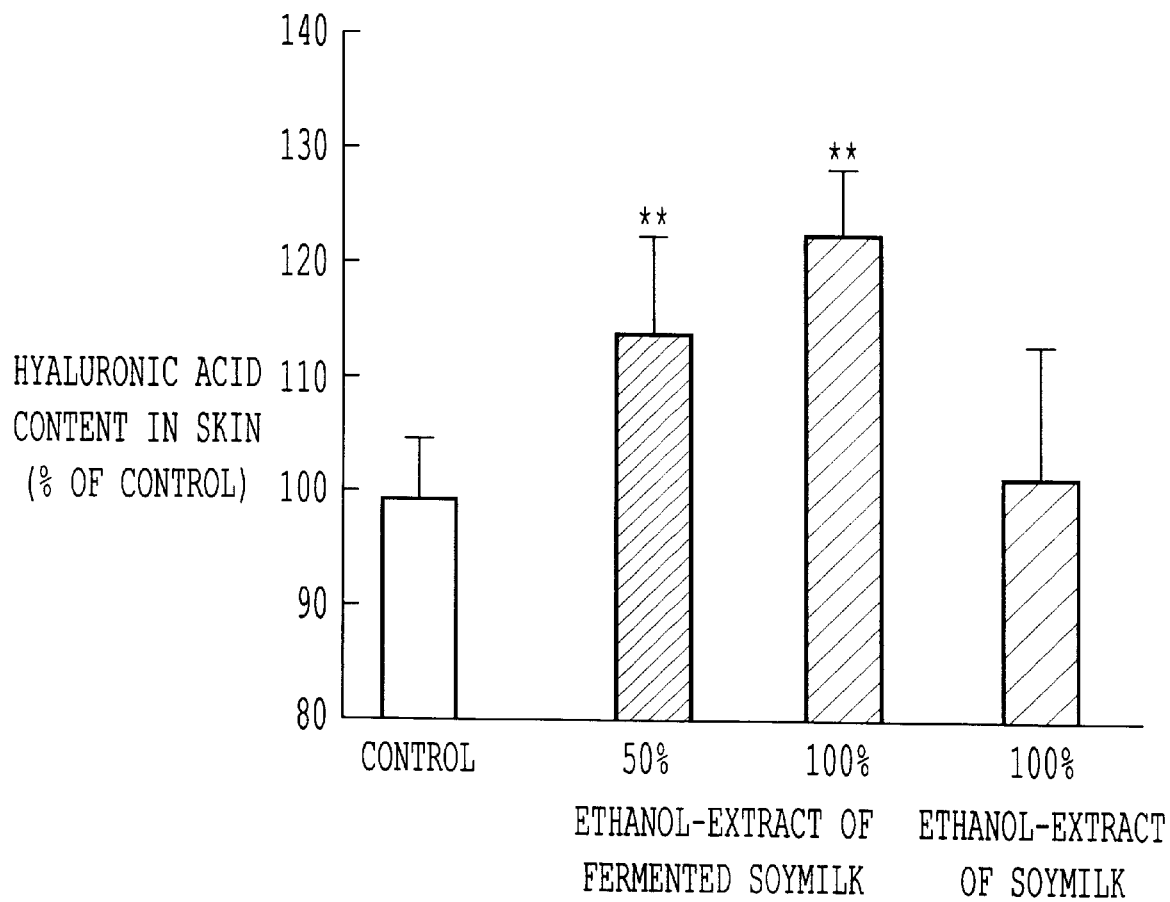
FIG. 3 is a graph showing the effect of a fermented soymilk extract on the hyaluronic acid content of the skin [mean±SD (n=3 or 6); *($p<0.05$) and **($p<0.01$): statistically significant with respect to the control (50% ethanol)].

As a result, it was found that application of a fermented soymilk extract significantly increases the hyaluronic acid content (FIG. 3). Increase in the hyaluronic acid content is considered to improve softness and elasticity of the skin.

A test similar to that described above was performed, using an extraction product with 1,3-butylene glycol prepared in Example 1. The results obtained are almost comparable to those obtained from the case in which ethanol was used for extraction.

Example 3

The lotion having the following composition was prepared by a routine method.

| | |
|---|---|
| Ethanol-extract of fermented soymilk (prepared in Example 1) | 1.0 wt. % |
| Ethanol | 10.0 wt. % |
| 1,3-Butylene glycol | 2.0 wt. % |
| Polyoxyethylene hydrogenated castor oil (50E.O.) | 0.05 wt. % |

-continued

| | |
|---|---|
| Methyl parahydroxybenzoate | 0.1 wt. % |
| Perfume | 0.1 wt. % |
| Purified water | balance |

The obtained lotion exhibited excellent rough skin ameliorating effect, and provided refreshing sensation during use. Storage stability was also satisfactory.

Example 4

The milky lotion having the following composition was prepared by a routine method.

| | |
|---|---|
| Ethanol-extract of fermented soymilk (prepared in Example 1) | 1.0 wt. % |
| Stearic acid | 2.0 wt. % |
| Liquid paraffin | 6.0 wt. % |
| Squalane | 2.0 wt. % |
| Sorbitan monostearate | 1.5 wt. % |
| Polyoxyethylene sorbitan monostearate (20E.O.) | 2.0 wt. % |
| Methyl parahydroxybenzoate | 0.05 wt. % |
| 1,3-Butylene glycol | 1.0 wt. % |
| Perfume | 0.15 wt. % |
| Purified water | balance |

The obtained milky lotion exhibited excellent wrinkle reversal effect, and provided moistened sensation during use. Storage stability was also satisfactory.

Example 5

The cream having the following composition was prepared by a routine method.

| | |
|---|---|
| Ethanol-extract of fermented soymilk (prepared in Example 1) | 1.0 wt. % |
| Liquid paraffin | 23.0 wt. % |
| Vaseline | 7.0 wt. % |
| Behenyl alcohol | 1.0 wt. % |
| Stearic acid | 2.0 wt. % |
| Beeswax | 2.0 wt. % |
| Sorbitan monostearate | 1.5 wt. % |
| Polyoxyethylene sorbitan monostearate (20E.O.) | 2.5 wt. % |

| -continued | |
|---|---|
| Butyl paraoxybenzoate | 0.05 wt. % |
| 1,3-Butylene glycol | 3.0 wt. % |
| Methyl parahydroxybenzoate | 0.1 wt. % |
| Perfume | 0.15 wt. % |
| Purified water | balance |

The obtained cream exhibited excellent wrinkle reversal effect, and provided excellent sensation during use. Storage stability was also satisfactory.

Example 6

The ointment having the following composition was prepared by a routine method.

| | |
|---|---|
| Ethanol-extract of fermented soymilk (prepared in Example 1) | 5.0 wt. % |
| Hydrophilic ointment (described in Japanese Pharmacopoeia) | 95.0 wt. % |

When the ointment was applied to wrinkle portions twice a day (2 mg/cm$^2$), excellent wrinkle reversal effect was observed. Storage stability was also satisfactory.

Industrial Applicability

The skin preparations for external use and cosmetic compositions according to the present invention exhibit excellent wrinkle reversal effect and rough skin ameliorating effect. Thus, the skin preparations and cosmetic compositions useful as an agent for retarding aging of the skin or an agent for ameliorating rough skin. Fermented soybean extract obtained through extraction with a specific polyhydric alcohol can be formed into skin preparations for external use endowed with excellent properties in terms of smell and sensation during use.

What is claimed is:

1. A skin preparation for external use in the form of a lotion, milky lotion, moisturizing cream, cleansing cream, massage cream, ointment or pack, comprising a fermented soybean extract prepared by extracting with an organic solvent a fermentation product obtained by treating a soybean extract with one or more microorganisms selected from bifidobacteria.

2. A skin preparation for external use according to claim 1, wherein the organic solvent is a C1–C13 monovalent or polyvalent alcohol.

3. A skin preparation for external use according to claim 1, which is a cosmetic composition.

4. A skin preparation for external use according to claim 1, which is a cosmetic composition for retarding aging of the skin or a cosmetic composition for ameliorating rough skin.

5. A skin preparation for external use comprising a fermented soybean extract prepared by extracting with an organic solvent a fermentation product obtained by treating a soybean extract with one or more microorganisms selected from bifidobacteria and further comprises at least one of a mucopolysaccharide, glycerol, a culture solution prepared by inoculating lactic acid bacteria into soy milk, a culture solution of lactic acid bacteria using milk ingredients, or a humectant.

6. A skin preparation for external use according to claim 5, wherein said mucopolysaccharide is hyaluronic acid.

7. A skin preparation for external use according to claim 5, wherein said humectant is pyrrolidone carboxylic acid, α-hydroxy acid or trimethylglycine.

8. A method for retarding aging of the skin or for ameliorating rough skin comprising applying to said skin the skin preparation according to claim 1.

* * * * *